United States Patent [19]

Stolowitz

[11] Patent Number: 5,399,317
[45] Date of Patent: Mar. 21, 1995

[54] REACTION CELL FOR PROTEIN SEQUENCER AND THE LIKE

[75] Inventor: Mark L. Stolowitz, Long Beach, Calif.

[73] Assignee: California Institute of Technology, Pasadena, Calif.

[21] Appl. No.: 93,059

[22] Filed: Jul. 16, 1993

[51] Int. Cl.[6] .......................................... B01L 11/00
[52] U.S. Cl. .................................. 422/99; 422/102; 935/86
[58] Field of Search ............... 422/70, 102, 68.1, 99; 935/85–88

[56] References Cited

U.S. PATENT DOCUMENTS

| | | | |
|---|---|---|---|
| 5,106,583 | 4/1992 | Raysberg et al. | 422/102 |
| 5,147,606 | 9/1992 | Charlton et al. | 422/102 |
| 5,188,968 | 2/1993 | Kano et al. | 422/102 |
| 5,200,152 | 4/1993 | Brown | 422/102 |

OTHER PUBLICATIONS

Reinke, H., Fischer, St., Reimann, F., and Tschesche, H., *Direct Microsequencing of Blotted and Covalently Attached Proteins in a Cross-Flow Reaction Chamber*, Methods in Protein Sequence Analysis, pp. 55–66, Birkhäuser Verlag, Basil, 1991.

Fischer, St., Reimann, Frank, and Wittmann-Liebold, Brigitte, 3.4 A New Modular Sequencer. 1989.

Sheer, D. G., Yuen, S., Wong, J., Wasson, J., and Yuan, P. M., *A Modified Reaction Cartridge for Direct Protein Sequencing on Polymeric Membranes*, BioTechniques, vol. 11, No. 4, pp. 526–533. Oct. 1991.

Totty, Nicholas F., Waterfield, Michael D., and Hsuan, J. Justin, *Accelerated High-sensitivity Microsequencing of Proteins and Peptides Using a Miniature Reaction Cartridge*, Protein Science, I, 1215–24, Cambridge University Press, 1992.

*Primary Examiner*—James C. Housel
*Assistant Examiner*—Rachel Heather Freed
*Attorney, Agent, or Firm*—Blakely, Sokoloff, Taylor, Zafman

[57] ABSTRACT

The present invention comprises a reaction cell for a sequencer and the like which includes a sample carrier assembly having a flexible, resilient spacer with a hole therein for retaining the sample on a membrane, a pair of alumina cells which bracket the spacer, one or more pads or spacers to retain the assembly in a tight fitting relation and a cap to secure the assembly together. The reagents are input and withdrawn from opposite edges of the sample membrane. The present invention has a minimal dead volume as a result of the spacer arrangement. It also permits benchtop sample loading due to the separation of the assembly into a carrier and base housing. The fluid lines are self-sealing to the reaction cell.

20 Claims, 6 Drawing Sheets

REACTION CELL FOR PROTEIN SEQUENCER AND THE LIKE

BACKGROUND OF THE INVENTION

1. Field Of The Invention

The present invention relates to an apparatus for the sequential degradation of proteins or polypeptides, and more particularly, to an improved reaction cell for containing small volumes of sample, and for greater control of the reactions therewithin. The reaction cell can be used for other biochemical processes as well.

2. Art Background

In 1957, P. Edman published a paper which began a new era in the field of protein sequencing, enabling eventually the automated sequencing of proteins and peptides in a liquid phase. P. Edman, Acta. Chem. Scand. 10,761(1957).

The three step process first involves coupling the N-terminal amino acid of a starting polypeptide to phenylisothiocyanate (PITC) in the presence of an acid scavenger in an alkaline aqueous or anhydrous solvent. The volatile excess reagent is removed in vacuo (homogeneous phase reaction) or by washing a polypeptide immobilized on an insoluble support (heterogeneous phase reaction) and byproducts of the reaction resulting from the decomposition of PITC are similarly removed, to yield the phenylthiocarbamyl (PTC) polypeptide.

In the second step, the PTC polypeptide is subjected to cleavage by a volatile anhydrous acid to afford the 2-anilino-5(4H)-thiazolinone (ATZ) of the N-terminal amino acid and the salt of the residual polypeptide, which is the starting polypeptide with the N-terminal amino acid removed.

The ATZ amino acid is extracted from the residual polypeptide or washed from the insoluble support in the cleavage acid which is subsequently removed in vacuo or evaporated under a stream of nitrogen gas at elevated temperature. In the third step, the ATZ amino acid, is ordinarily subjected to conversion to the more stable phenylthiohydantoin (PTH) amino acid. The conversion reaction can be effected thermally or by heating the ATZ amino acid in aqueous, methanolic or anhydrous acid.

The resultant PTH amino acid is identified chromatographically while the shortened residual polypeptide is neutralized and then reacted with PITC to initiate the next cycle of degradation. The foregoing steps (coupling, cleavage and conversion) are repeated for each N-terminal amino acid in the polypeptide.

In 1967 Edman taught in, Edman et al., "A Protein Sequenator" European J.Biochem. 1 (1967) 80–91 a "spinning cup" automated sequencer which permitted the automated sequencing of peptides, still using a liquid phase separation.

In the late 1960's and early 1970's, a modification of the basic Edman chemistry was developed which involved the concepts of Edman degradation as applied using solid phase chemistry. These developments, pioneered by Richard Laursen, Eur.J. Biochem 20 (1971) 89–102 "Solid Phase Edman Degradation-An Automatic Peptide Sequencer" enabled researchers to bind the protein or peptide to be sequenced onto a solid resin, and to pump the Edman reagents past the bound peptide to provide the chemistry that sequentially degraded the peptide.

Further developments to this process were made by Dreyer, U.S. Pat. No. 4,065,412 which disclosed the use of macroporous beads to which a sample of protein or peptide is bound by chemical coupling or direct adsorption, the beads being disposed within a reaction column.

Hood, et al. in U.S. Pat. Nos. 4,252,769, 4,603,114 and 4,704,256 discloses methods and apparatus for sequential degradation of proteins and peptides by binding the samples onto a solid matrix of fluid permeable material located in a reaction chamber and applying a pressurized stream of chemicals sequentially to perform the Edman chemistry.

The emphasis at the present time is in the development of chemistries and apparatus which is substantially more sensitive, faster and in some instances, less expensive than prior art systems. The first parameter of sensitivity is particularly critical since many of the prior art methods are not entirely satisfactory in the microsequencing of small amounts of protein.

Many physiologically active proteins are present in organisms at such extremely small concentrations that only very small amounts of the proteins can be obtained for sequencing analysis. The current techniques described in the literature are aiming to obtain sensitive detecting in the picomole range. Hunkapiller and Hood, "Protein Sequence Analysis: Automated Microsequencing", Science 219 (1983) 650–659 teaches automated sequencing in the 5 to 10 picomole range.

In 1985, Hawke, Harris, and Shively, "Microsequence Analysis of Peptides and Proteins V. Design and Performance of a Novel Gas-Liquid-Solid Phase Instrument" Analytical Biochemistry 147 315–330 (1985) published an article describing an apparatus for microsequencing. This device was taken the next step by Calaycay, Rusnak and Shively, "Microsequence Analysis of Peptides and Proteins-IX. An Improved Compact Automated Instrument" Analytical Biochemistry 192 23–31 (1991) which teaches a sequencer with a sensitivity in the same range (5–10 picomoles), and a valve which is useful for microsequencing. The sequencer has a vertical flow path and a continuous flow reactor and includes a hexagonal valve for six fluid inputs to the reactor which allows sample, reagent and solvent input into a conversion flask containing two inputs on top and a drain on the bottom, the drain connecting to a valve which can connect the flask to either a waste flask or an on-line HPLC for the analysis of the PTH amino acid derivatives.

Most recently, several companies have introduced sequencers intended to handle the requirements of microsequencing, including Applied Biosystems (Protein/Peptide Sequencer PTH Analyzer 477A/120A, 473 and 476) and Milligen/ Biosearch Div. of Millipore (Prosequencer TM ). Notwithstanding these efforts, successful consistent sequencing in the femtomole range has not yet been achieved. Moreover, the cost of these prior art devices remains substantial, making such devices unattainable for smaller laboratories.

A recent development in sequencer reaction chambers has been described by Fischer in his EPO patent No. 526691 issued February 1993. The reaction chamber is in the form of a shallow recess with an inlet and outlet at each end of the recess. The recess houses a filter element which has a sample absorbed thereon, and the reagents flow from the inlet, through or across the filter and out of the outlet. The Fischer cross-flow reaction chamber has also been described in Method of Protein Sequence Analysis, "Direct Microsequencing of Blotted and Covalently Attached Proteins in a Cross- Flow Reaction Chamber," Reinke, et al., 1991, Birkhauser Verlag Basel.

Another current reaction vessel is the type used in Applied Biosystem sequencers described in "A Modified Reaction Cartridge for Direct Protein Sequencing on Polymeric Membranes", Sheer, et al., Biotechniques, Vol. 11, No. 4, p. 526 et seq. This article describes Applied Biosystem's vertical cross-flow reaction cartridge for sequencing, made of two mating cylindrical blocks of glass with a bore through the central axis of each, and a recess in the lower block to hold a membrane. The volume of this reaction vessel can be as small as 120 microliters.

The present invention attempts to overcome some of the problems with the prior art devices in providing a reaction cell for microsequencing having a substantially smaller volume, and particularly a small dead volume which enables the sequencing of smaller amounts of protein or polypeptides. The invention can also be used to sequence DNA/RNA, and can be used in synthetic processes as well without substantial modification.

SUMMARY OF THE INVENTION

The present invention comprises a novel reaction chamber adapted for use in a protein sequencer, although it can be used in other automated biochemical processors as well. The present invention offers the opportunity for optimized rapid and highly sensitive Edman and alternative biochemical degradations.

The present invention comprises a sample carrier assembly which includes a flexible, resilient spacer with a hole therein for retaining the sample on a membrane, a pair of alumina cells which bracket the spacer, one or more pads or spacers to retain the assembly in a tight fitting relation and a cap to secure the assembly together. The reagents are input and withdrawn from opposite edges of the sample membrane. The input and outline lines are spring loaded against the assembly to provide a relatively fluid tight arrangement which is easy to assemble. The base assembly which includes the circuit board, aluminum block and heating elements is easily separable from the sample carrier which comprises the alumina cells, spacer, cap and washer, so that the sample can be loaded into the sample carrier on a bench top, and then the sample carrier can be easily connected to the base assembly. This overcomes the problems of the prior art systems which typically require that the sample be loaded directly onto the sequencer, and does not permit loading on the benchtop.

The spacer can be of varying shape and size to accomodate different size samples. The spacer is made of virgin Teflon and is preferably laser cut to provide a very flat and regular surface. As a result, there is little opportunity for the sample carrier to leak, even under pressure. For larger samples, several spacers can be stacked together in order to provide a larger volume. Also, the spacers can be provided with holes of different geometries for specialized purposes. The spacers allow for maximum variation in the operation of a sequencer in accordance with the present invention at minimal cost because the spacers are relatively inexpensive, as compared with other systems which require extensive modification or expensive additions to make small changes in the geometry of the reaction cells.

The present invention also provides, in the preferred embodiment, a fast and efficient heating system in the form of a pair of heating coils embedded into an aluminum block to which the sample carrier is attached. A safety power cutoff is also provided in the event that the temperature exceeds a predetermined limit. The aluminum block is electrically and thermally isolated from a circuit board which houses some of the electrical controls and interfaces, as well as the light source.

In accordance with the summary of the invention set forth above, and the detailed description and accompanying drawings, it is an object of the present invention to provide a reaction cell for the sequential degradation of proteins and peptides.

It is another object of the present invention to provide a reaction cell which may be used in a protein sequencer for identification of amino acids through Edman degradation or other protein degradation chemistry in the femtomole range.

It is another object of the present invention to provide a reaction cell for a sequencer which utilizes minimal amounts of reagents.

It is another object of the present invention to provide a reaction cell in which the volume of the reaction chamber is related to the size and geometry of the spacer, or spacers.

These and other objects of the present invention will be understood with reference to the detailed description herein and the accompanying drawings.

DETAILED DESCRIPTION OF THE INVENTION

The present invention, as shown in FIGS. 1-2, 4 and 8, is a reaction cell assembly for a protein sequencer which accommodates protein samples for sequencing. In general, while the figures show the invention in a vertical configuration, which is a possible arrangement for the present invention, the reaction cell of the present invention will often be in a horizontal configuration. It will be understood by persons of skill in the art that variations in the orientation can be accomplished without undue experimentation, and are known in the art to accomplish different effects.

Figure 1:
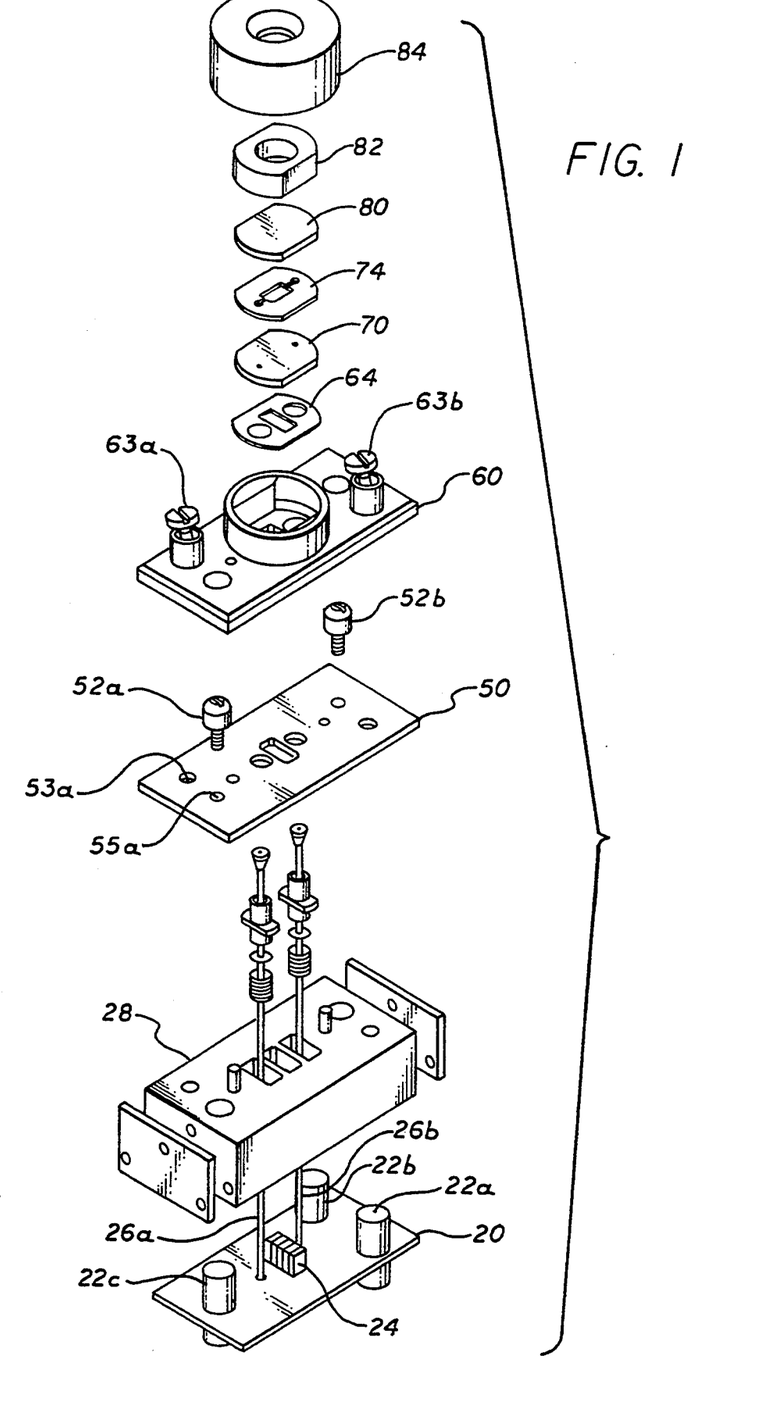
FIG. 1 is an exploded view of a reaction cell assembly of the present invention.
Figure 2:
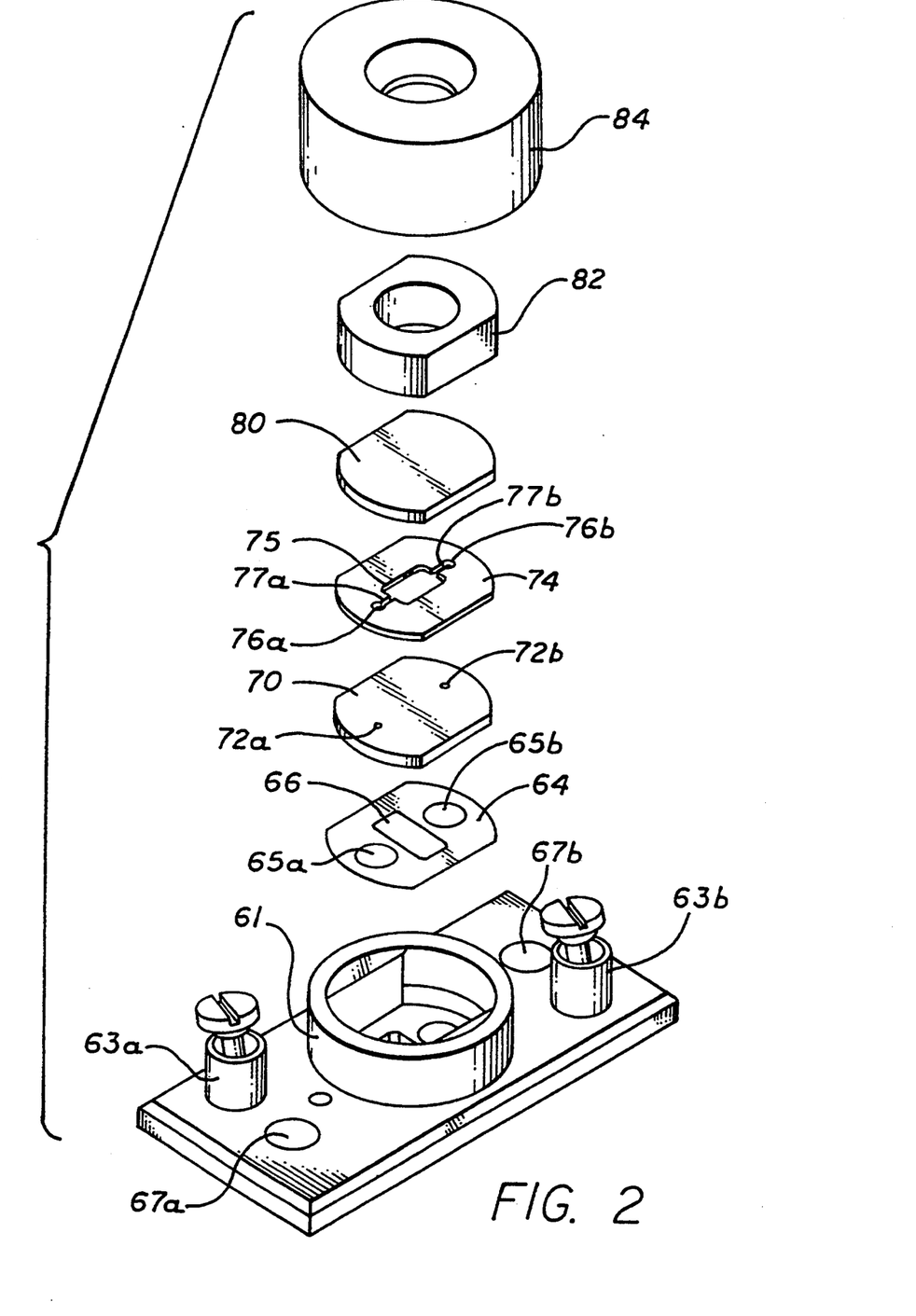
FIG. 2 is an enlarged exploded view of the top portion of the reaction cell assembly of the present invention.

Now referring to FIGS. 1, 2 and 4, starting from the bottom there is a circuit board 20 having a plurality of support posts 22a, 22b, and 22c thereon which also act to space the block 28 from the circuit board 20 and electrically and thermally insulate the two. Thermal insulation is important primarily because the LEDs are temperature sensitive, and failure occurs with present LEDs at temperatures above 80° C. Thus, an over temperature fuse is supplied (not shown) for a temperature cutoff of 100° C. Other fuses may be selected, however. There is also an LED light display bank 24 to light the reaction chamber to see what is occuring therein. Also shown are the reagent lines 26a and 26b which provide the reagents and other fluids to the sample in accordance with the requirements of the particular sequencing steps. The reagent lines 26a and 26b are preferably made of Teflon ® and preferably have an inside diameter of 0.030 inches. The LEDs 24 may be electrically connected to a variable control which controls the intensity of the light.

Figure 3:
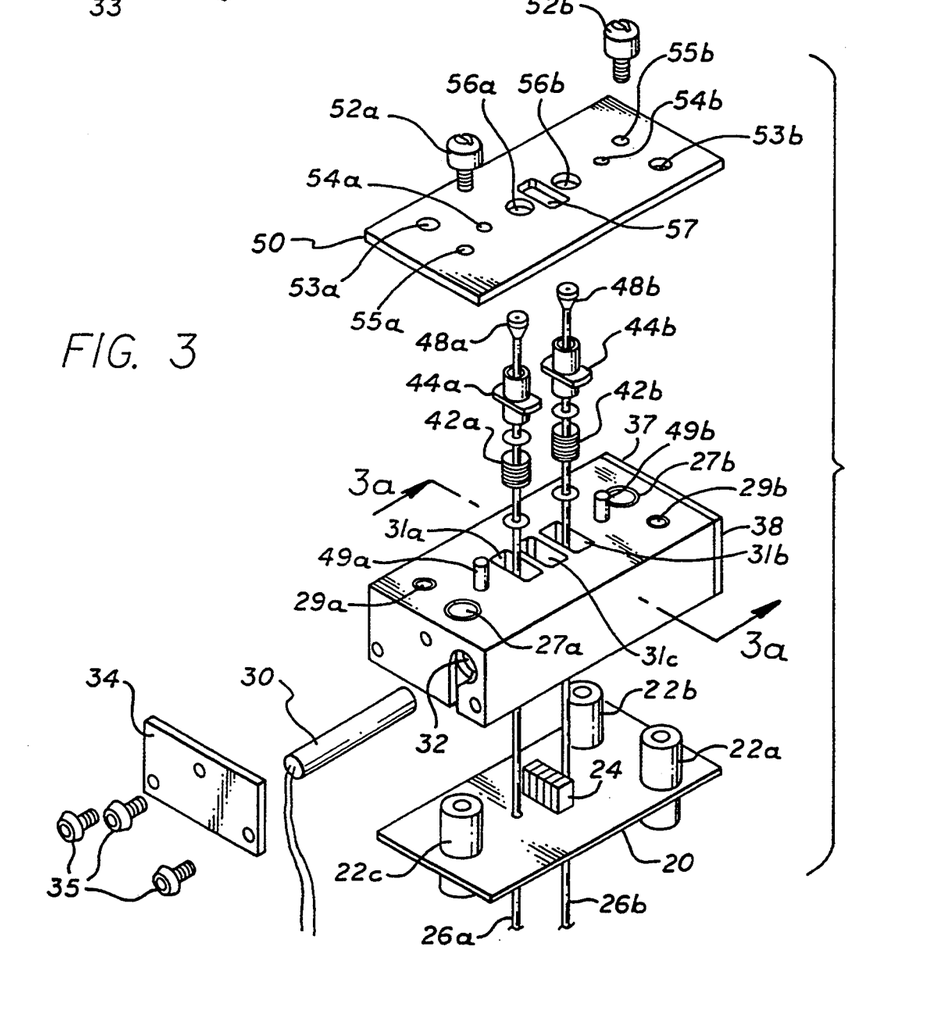
FIG. 3 is an enlarged exploded view of the bottom portion of the reaction cell assembly of the present invention.
Figure 3A:
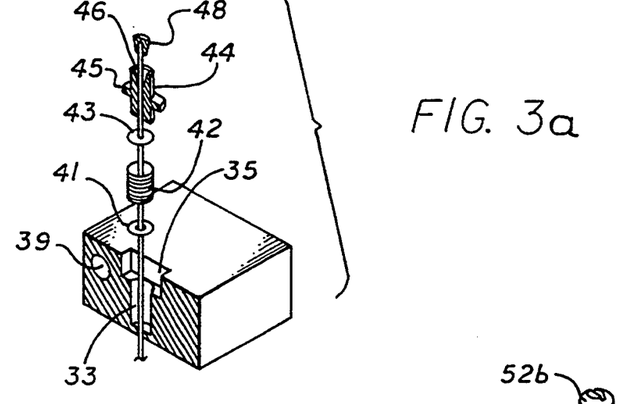
FIG. 3a is a transverse sectional view of the block of the reaction cell assembly taken through lines 3a—3a of FIG. 3.

At the next level is the block 28 which is preferably made out of aluminum or other thermally conductive material. A heater assembly 30 is disposed through a hole 32 in the block and is designed to heat the system to the desired temperature to control the temperature at which the reactions occuring in the reaction cell assembly of the present invention occur. The heater is preferably linear within the temperature range of 25° C. and 75° C. and is controllable withing 0.1° C. It is preferably operated on 24 V DC at 15 watts. It is capable of raising the temperature of the alumina block about 20° C. per minute. Other heaters can be used if the maximum temperature needs to exceed 75° C., and it is known that heaters of up to 150° C. may be required for some applications. The heater is held in the block 28 by a side plate 34 which is held to the block by screws 35. The opposite side 37 is similarly constructed with a side plate 38 holding a heater (not shown) in a hole 39 shown in FIG. 3a. As shown in the top of block 28 there are three rectangular holes. Holes 31a and 31b are to permit the flow lines 26a and 26b to pass therethrough and hole 31c in the middle permits the light from the LED display bank 24 to pass through to the sample as described below for illumination of the sample. Since the block is made of aluminum, a relatively soft metal, all screws into the block are actually screwed into tapped stainless steel inserts.

The flow lines 26a and 26b are held be spring pressure to the sample. The spring assembly can best be understood in FIGS. 3 and 3a. Hole 31b has a narrow cylindrical portion 33 and an enlarged rectangular portion 35. A washer 41, spring 42 and second washer 43 are disposed in the narrow cylindrical portion 33. A flow line head holder 44 having a generally cylindrical shape with a collar 45 is disposed in the large rectangular portion 35. The top of the flow line head holder has a cup-shaped recess 46 which mates with the flow line head 48. Flow line head 48 is preferably made of Kel-F ® (DuPont). The spring 42 causes the flow line head 48 to press against the alumina cell, making a fluid tight seal, at a pressure of about 30 psi. This is the standard maximum pump pressure for commercially available sequencers, and thus, provides sufficient sealing for standard operation. Obviously greater pressure could be applied by the selection of a stiffer spring, if desired.

Also on the top surface of the block 28 is a pair of alignment pins 49 which allow for alignment of the block to the spring plate 50 and sample carrier 60. The spring plate 50 is held to the block 28 by screws 52a and 52b going through holes 55a and 55b respectively. The alignment pins 49a and 49b pass through holes 54a and 54b in the spring plate. Circular holes 56a and 56b are adapted to receive flow line heads 48a and 48b. Rectangular hole 57 permits the light from LED bank 24 to pass through. Holes 53a and 53b permit assembly screws 63a and 63b to pass through to the block 28, and particularly, to screw into holes 29a and 29b.

The next level is the sample carrier 60, shown in FIGS. 1 and 2. The sample carrier 60 has a sample holding assembly comprising a collar 61. Inside the collar 61 is disposed a Sil-Pad TM (Silicone coated fiberglass pad made by Burquest) 64, which is thermally conductive and electrically insulative, inner alumina cell 70 which is transparent, TFE (teflon) spacer 74, outer alumina cell 80 which is transparent, TFE teflon washer 82 and PEEK (polyethylene ethylketone) cap 84 which fits over the collar and through the washer 82 holds the cell together. The inner and outer alumina cells, 70 and 80 sandwich the TFE (teflon) spacer 74 which will hold the sample (not shown) in the hole 75 therein on a membrane (also not shown). Thus, an essentially water-tight seal is created between the two alumina cells for the reactions for sequencing to occur, and reagents to be supplied to the sample on the membrane. Holes 65a and 65b permit the flow line heads 48a and 48b to pass through, and hole 66 permits the light from the LED bank 24 to pass through to the sample, illuminating the sample so that the sample may be viewed. Flow line heads 48a and 48b are removable and replacable, and can be crimped onto the fluid lines 26a and 26b for easy replacement.

Holes 72a and 72b in inner alumina cell 70 permits the fluid in the flow lines 26a or 26b to enter the area between the two alumina cells 70 and 80 to contact the sample, and to be withdrawn from the outlet flow line (the other of either 26a and 26b). For convenience, we will refer to line 26a as the inlet line and 26b as the outlet line.

In assembling the present invention, the fluid lines 26a and 26b can be fed through the aluminum block before the sample carrier is installed on the block. This arrangement makes for easy assembly. The spring loaded fluid lines are then provided with a pressurized seal to the sample carrier.

Figure 6:
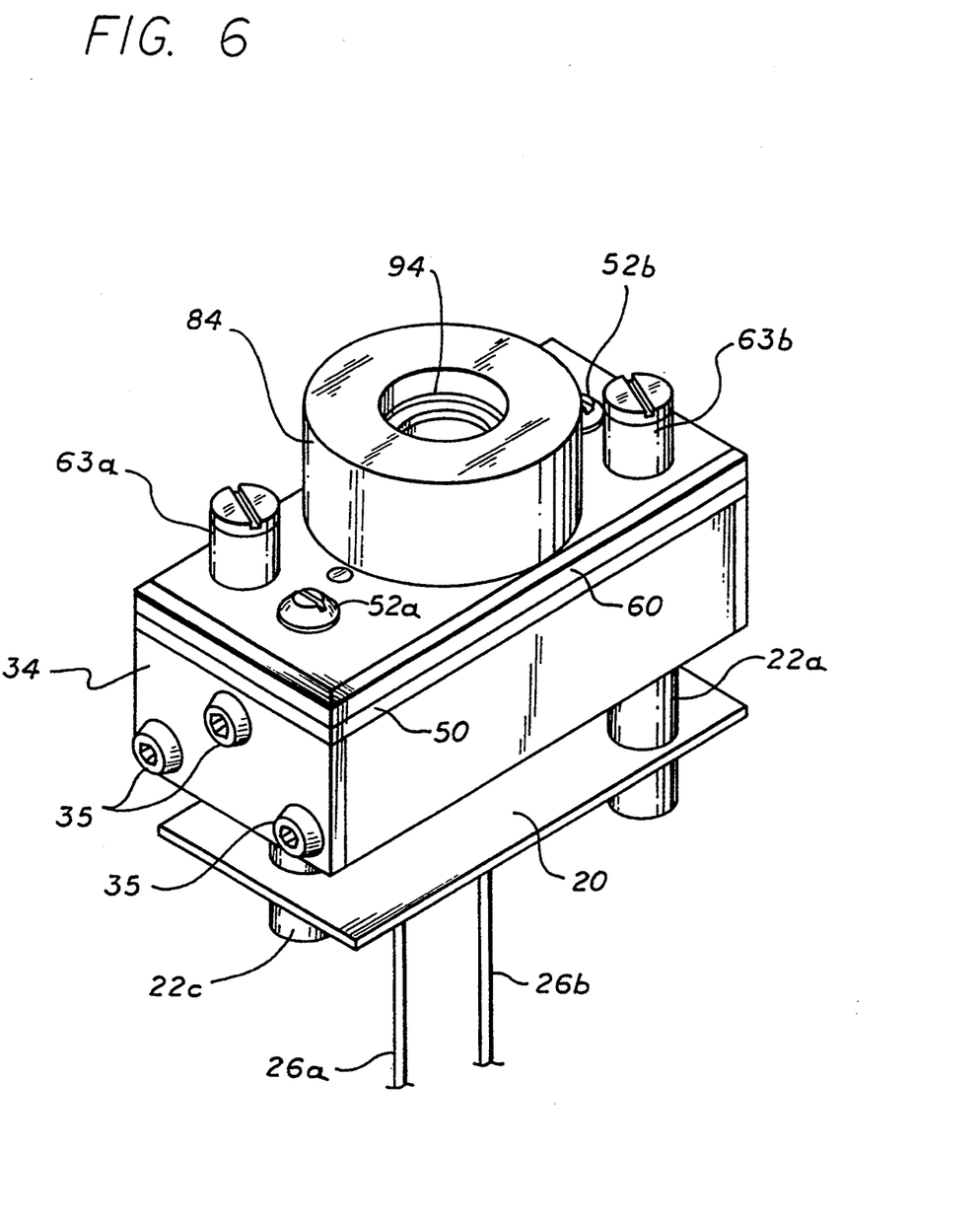
FIG. 6 is a perspective view of the assembled reaction chamber assembly of the present invention.

FIG. 6 shows the assembled reaction cell assembly of the present invention. A magnifying glass 94 may be disposed at the top to permit enlarged viewing of the sample in the reaction cell.

The TFE spacer has a cutout 75 with holes 76a and 76b to receive the fluid in the flow line 26a and withdraw it from line 26b after it has passed through the sample, and channels 77a and 77b which are on opposite sides of the cutout, and are aligned with holes 76a and 76b, respectfully, and are in fluid communication with cutout 75.

Figure 4A:
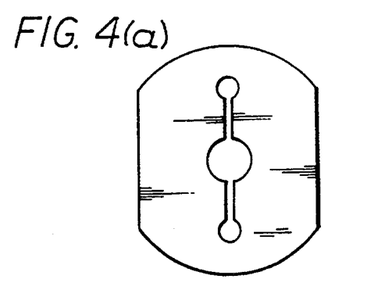
FIG. 4(a)-4(d) is a top plan view of 4 different spacers which accommodate different sample sizes in the reaction cell assembly of the present invention.

FIG. 4(a) is a spacer for a sample for a single protein spot from a 2D electrophoretic gel having a diameter in the range of 4–4.5 millimeters.

Figure 4B:
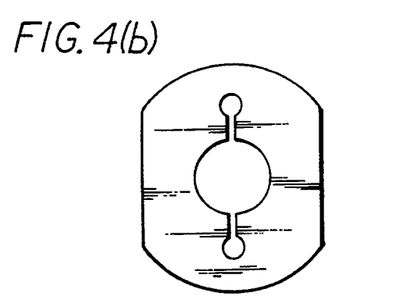

FIG. 4(b) is a spacer for a sample on a standard commercially available membrane typically used in a solid phase sequencer; the membrane has a diameter of about 7.5 mm, and the hole in the spacer has a diameter of about 8.5 mm.

Figure 4C:
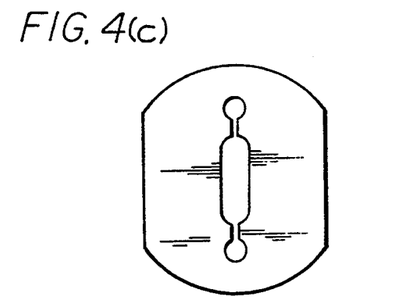

FIG. 4(c) is a spacer for a sample taken from a Western blot from a single lane of a slab gel; it has a length of about 10 mm and a width of about 0.7 mm.

Figure 4D:
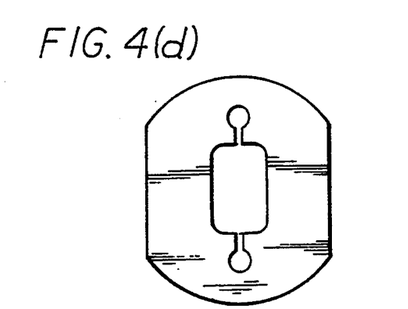
Figure 5A:
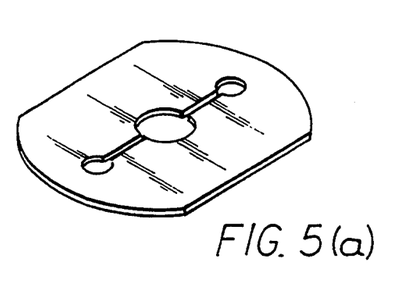
FIG. 5(a)-5(d) is a perspective view of each of the spacers in FIGS. 4(a)-4(d).
Figure 5B:
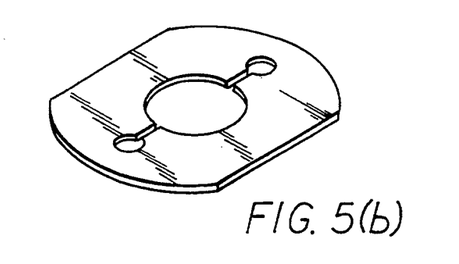
Figure 5C:
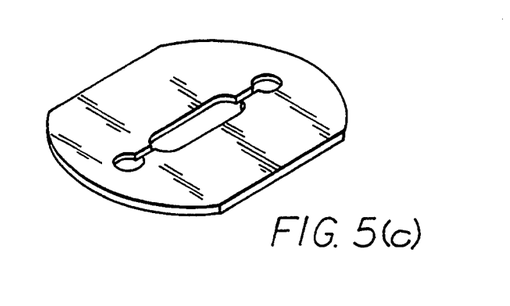
Figure 5D:
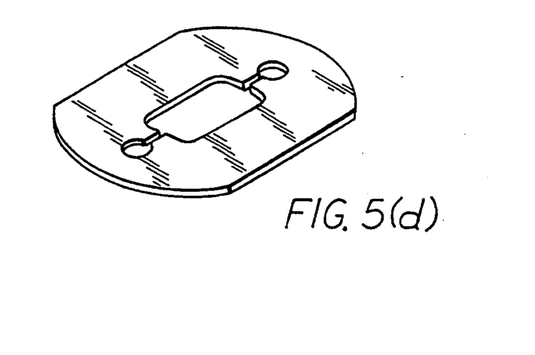

FIG. 4(d) is a spacer for a sample taken from a Western blot from three to four lanes of a slab gel; it has a length of about 10 mm and a width of about 0.7 mm.

Each spacer is made of virgin Teflon ®, and is 0.8 mm (1/32 of an inch) thick. As shown in FIGS. 4 and 5, the shape and size of the holes varies for different sample sizes. The overall width of the spacers is about 20 mm and the distance between the center of the first hole 65a to the second hole 65b is about 16 mm for each of the spacers. Each hole has a diameter of about 2.5 mm. The outer periphery of the spacer is shaped to fit securely in the sample carrier so that there is proper alignment of the holes 65a and 65b with the flow lines. As can be seen the holes 65a and 65b are connected to the cutout 75 to permit flow of the reagent liquids in the flow lines. It is important that the spacers be made of an unmarred material, such as virgin Teflon, because a fluid tight seal is essential for the small volumes of fluids being used with this assembly. The spacers are preferably laser cut, because even die cut spacers are not sufficiently flat for the invention to properly function. The spacers must be made out of a chemically inert material, and provide a uniform sealing face since they act as a gasket to seal the volume between the two alumina cells.

The dead volume of the present invention is about 7 to 14.5 microliters depending upon the spacer used, about an order of magnitude smaller than currently available prior art systems.

Figure 7:
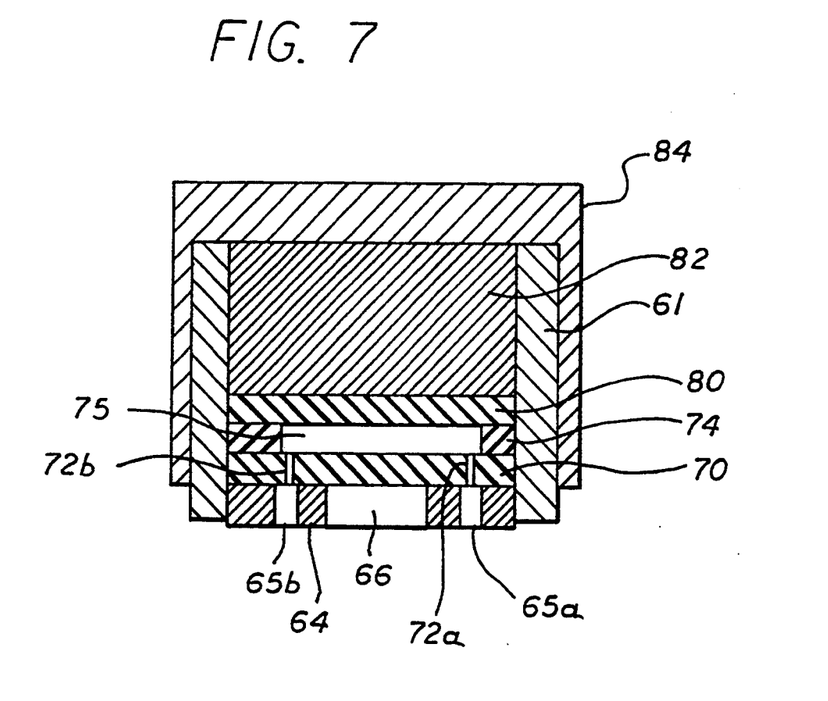
FIG. 7 is a side cross-sectional view of the sample carrier of the present invention.

As shown in FIG. 7, which is a cross-sectional view of a sample carrier assembled, the arrangement of the carrier includes the cap 84, piston 82, outer alumina cell 80, spacer 74, inner alumina cell 70, and Sil-Pad TM (Silicone coated fiberglass pad made by Burquest) 64 which all sit within the carder. The holes 65a and 65b align in the Sil-Pad TM (Silicone coated fiberglass pad made by Burquest) 64 with the small holes 72a and 72b in the inner alumina cell 70, which will provide a fluid path for reagents and the like to the sample through holes 76a and 76b.

Figure 8:
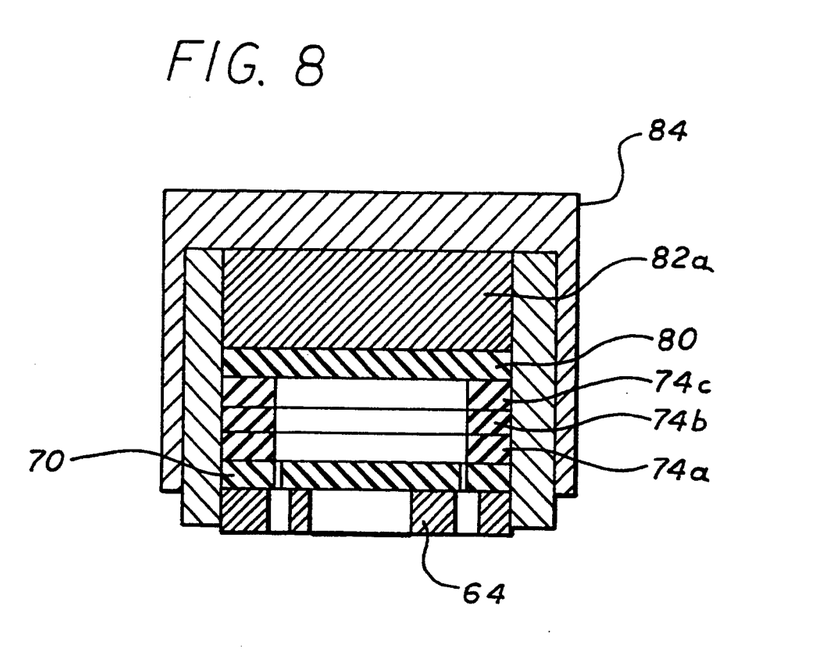
FIG. 8 is a side cross-sectional view of a sample carrier of an alternative embodiment containing a stack of multiple spacers.

As shown in FIG. 8, a plurality of spacers 74a, 74b and 74c can be stacked. In that case, a smaller piston 82a is used.

It will be obvious to a person of ordinary skill in the art that numerous modifications and changes can be made to the above processes and apparatus in order to accomplish the same function without departing from the spirit and scope of the present invention.

I claim:

1. A reaction chamber assembly comprising:
   a pair of chemically inert, transparent plates, one of said plates having a plurality of holes for the input and outlet of fluids; and
   a flat spacer means disposed between said plates and formed from an inert material, said spacer means having a cutout defining a volume in which to place a sample, and a plurality of channels, each of said plurality of channels being aligned with one of said plurality of holes in said plate, said plurality of channels being in fluid communication with said cutout; and
   sample carrier with a cylindrical collar, wherein said plates and said spacer are disposed inside said cylindrical collar.

2. The reaction chamber assembly claim 1 wherein said spacer means comprises virgin polytetrafluoroethylene.

3. The reaction chamber assembly of claim 1 wherein said plurality of channels comprise two channels, which are disposed on opposite sides of said cutout, and said plurality of holes comprises two holes.

4. The reaction chamber assembly of claim 1 wherein said assembly has a dead volume of less than 15 microliters and greater than zero microliters.

5. The reaction chamber assembly of claim 1 further comprising a plurality of spacer means stacked together with the cutouts of each of said spacer means being aligned to form the volume to retain a sample.

6. The reaction chamber assembly of claim 5, further comprising a number of spacer means, and a washer for securing said plates together under sufficient pressure to prevent leaks therein, said washer being sized relative to the number of spacer means.

7. The reaction chamber assembly of claim 1 further comprising a heating block to which the sample carrier is attached.

8. The reaction chamber assembly of claim 7 wherein a portion the reaction chamber assembly comprises a removable portion and a fixed portion, and said removable portion is removable from the remainder to load a sample therein before assembly to said fixed portion.

9. The reaction chamber assembly of claim 8 further comprising fluid lines aligned with said holes in said plate, flow line head holders which are disposed around the end of each fluid line and spring wherein said springs push said flow line head holders against said plate to form a fluid tight seal around said holes in said plate when said reaction chamber is assembled.

10. The reaction chamber assembly of claim 1 further comprising a light source for illuminating the sample.

11. The reaction chamber assembly of claim 1 further comprising a light source, wherein said plates and said spacer of said reaction chamber permit light from said light source to illuminate the sample for viewing of said illuminated sample.

12. A reaction chamber assembly comprising: a sample carrier comprising a housing including a plate having a cylindrical cavity, said sample carrier further comprising:
   a cap means removably coupled to said cylindrical cavity sample carrier;
   a washer disposed adjacent said cap;
   a first inert transparent flat plate disposed adjacent said washer;
   at least one flat spacer having a cutout therein with a channel extending from opposite ends of said cutout, wherein said flat space is disposed adjacent said first plate; and
   a second inert transparent flat plate having holes therein aligned with the ends of said channels, which are furthest from said cutout, said first flat plate, and second flat plate forming a fluid tight seal around the edges of the spacer, and defining an inlet and outlet by said holes; and
   a base house to which the sample carrier is attached, and wherein said base housing fixed to a sequencer, said base housing comprising:
   a heating block; which contacts the sample carrier when said sample carrier is attached to said base housing;
   a circuit board means including a light source; and
   a thermal insulating means disposed between said heating block and said circuit board; wherein said circuit board means is separated from said heating block by said thermal insulating means.

13. The reaction chamber of claim 12 further comprising an inlet and outlet fluid line being spring biased against said second plate to form a fluid tight seal around said holes in said second plate.

14. The reaction chamber assembly of claim 12 wherein said spring bias is at approximately 30 pounds per square inch.

15. The reaction chamber assembly of claim 12 wherein said fluid line has a bushing disposed on the end thereof.

16. The reaction chamber assembly of claim 12 wherein said at least one flat spacer comprises a plurality of spacers, and said washer is size selected to provide a sufficient pressure to cause said plates and said spacers to form a fluid tight seal.

17. The reaction chamber assembly of claim 12 wherein said plates are made of alumina.

18. The reaction chamber assembly of claim 12 further comprising an electrically conductive, thermally insulative pad disposed between said second plate and said housing of said sample carrier.

19. The reaction chamber assembly of claim 12 wherein said cutout is capable of being custom sized to accomodate a sample of any size and shape.

20. The reaction chamber assembly of claim 12 wherein said circuit board is set off from said heating block.

* * * * *